US00PP30783P2

(12) United States Plant Patent
Beekenkamp

(10) Patent No.: US PP30,783 P2
(45) Date of Patent: Aug. 6, 2019

(54) ***BEGONIA* PLANT NAMED 'BKPBEENS'**

(50) Latin Name: ***Begonia* x *hiemalis***
Varietal Denomination: Bkpbeens

(71) Applicant: Annie Cornelia Beekenkamp, Maasdijk (NL)

(72) Inventor: Annie Cornelia Beekenkamp, Maasdijk (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 15/732,949

(22) Filed: Jan. 12, 2018

(51) Int. Cl.
*A01H 5/02* (2018.01)

(52) U.S. Cl.
USPC ..... Plt./349
CPC ..... *A01H 5/02* (2013.01)

(58) Field of Classification Search
USPC ..... Plt./349
See application file for complete search history.

*Primary Examiner* — Anne Marie Grunberg
(74) *Attorney, Agent, or Firm* — C. A. Whealy

(57) ABSTRACT

A new and distinct cultivar of *Begonia* plant named 'Bkpbeens', characterized by its broadly upright to outwardly spreading and mounded plant habit; sturdy plants with freely basal branching habit; dark green-colored leaves; uniform and freely flowering habit; and double flowers that are light red in color.

2 Drawing Sheets

Botanical designation: *Begonia* x *hiemalis*.
Cultivar denomination: 'BKPBEENS'.

BACKGROUND OF THE INVENTION

The present invention relates to a new and distinct cultivar of *Begonia* plant, botanically known as *Begonia* x *hiemalis*, commercially referred to as Elatior *Begonia* and hereinafter referred to by the name 'Bkpbeens'.

The new *Begonia* plant is a naturally-occurring whole plant mutation of *Begonia* x *hiemalis* 'Batik', not patented. The new *Begonia* plant was discovered and selected by the Inventor as a single flowering plant from within a population of plants of 'Batik' in a controlled greenhouse environment in Landau, Germany in August, 2015.

Asexual reproduction of the new *Begonia* plant by vegetative tip cuttings in a controlled greenhouse environment in Maasdijk, The Netherlands since June, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Bkpbeens'. These characteristics in combination distinguish 'Bkpbeens' as a new and distinct *Begonia* plant:

1. Broadly upright to outwardly spreading and mounded plant habit.
2. Sturdy plants with freely basal branching habit.
3. Dark green-colored leaves.
4. Uniform and freely flowering habit.
5. Double flowers that are light red in color.

Plants of the new *Begonia* can be compared to plants of the mutation parent, 'Batik'. Plants of the new *Begonia* differ primarily from plants of 'Batik' in the following characteristics:

1. Flowers of plants of the new *Begonia* are double in form whereas flowers of plants of 'Batik' are semi-double in form.
2. Plants of the new *Begonia* and 'Batik' differ in flower color as plants of 'Batik' have bright orange-colored flowers.

Plants of the new *Begonia* can be compared to plants of *Begonia* x *hiemalis* 'Bkpbeegl', disclosed in U.S. Plant Pat. No. 23,825. Plants of the new *Begonia* differ primarily from plants of 'Bkpbeegl' in the following characteristics:

1. Outer tepals of plants of the new *Begonia* have entire margins whereas outer tepal margins of plants of 'Bkpbeegl' are incised.
2. Plants of the new *Begonia* and 'Bkpbeegl' differ in flower color as plants of 'Bkpbeegl' have bright pink-colored flowers.

Plants of the new *Begonia* can also be compared to plants of *Begonia* x *hiemalis* 'Nelly', not patented. Plants of the new *Begonia* differ primarily from plants of 'Nelly' in the following characteristics:

1. Flowers of plants of the new *Begonia* are double in form whereas flowers of plants of 'Nelly' are single to semi-double in form.
2. Plants of the new *Begonia* and 'Nelly' differ in flower color as plants of 'Nelly' have salmon pink-colored flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Bkpbeens' grown in a container.

The photograph on the second sheet are close-up views of a typical flower bud and the upper and lower surfaces of typical developed flowers and leaves of 'Bkpbeens'.

DETAILED BOTANICAL DESCRIPTION

Plants used for the aforementioned photographs and following observations and measurements were grown during the autumn in 12-cm containers in a glass-covered greenhouse in Maasdijk, The Netherlands. During the production of the plants, day and night temperatures ranged from 19° to 21° C. Plants were eight weeks from planting rooted cuttings when the photographs and the description were taken. In the following description, color references are made to The Royal Horticultural Society Colour Chart, 2015 Edition, except where general terms of ordinary dictionary significance are used.

Botanical classification: *Begonia* x *hiemalis* 'Bkpbeens'.

Parentage: Naturally-occurring whole plant mutation of *Begonia hiemalis* 'Batik', not patented.

Propagation:

*Type*.—By vegetative tip cuttings.

*Time to initiate roots*.—About 20 days at temperatures about 25° C.

*Time to produce a rooted young plant*.—About 35 to 36 days at temperatures about 21° C. to 23° C.

*Root description*.—Fine, fibrous; typically brown in color, actual color of the roots is dependent on substrate composition, water quality, fertilizer type and formulation, substrate temperature and physiological age of roots; plants of the new *Begonia* have not been observed to form tubers.

*Rooting habit*.—Freely branching habit; medium density.

Plant description:

*Plant and growth habit*.—Broadly upright to outwardly spreading and mounded plant habit; overall plant shape, broadly obovate; moderately vigorous growth habit; moderate growth rate.

*Plant height, soil level to top of foliar plane*.—About 22.3 cm.

*Plant height, soil level to top of floral plane*.—About 24.7 cm.

*Plant width*.—About 36.4 cm.

*Lateral branch description*.—Branching habit: Freely branching habit with about four basal branches developing per plant; pinching is not required. Length: About 11.6 cm. Diameter: About 8 mm to 9 mm. Internode length: About 2.9 cm. Strength: Moderately strong. Aspect: About 30° from vertical. Texture and luster, young stems: Sparsely to moderately pubescent; slightly glossy. Texture and luster, developed stems: Smooth, glabrous; slightly glossy. Color, developing: Close to 146C; at the internodes, close to 185A. Color, fully developed: Close to 148B.

*Leaf description*.—Arrangement: Alternate, simple. Length: About 14.9 cm. Width: About 10.7 cm. Shape: Ovate, unequal. Apex: Acute. Base: Oblique, lobes meeting to slightly imbricate. Margin: Serrate to dentate; moderately to strongly and coarsely undulate. Texture and luster, upper surface: Smooth, glabrous; velvety; slightly glossy. Texture and luster, lower surface: Sparsely pubescent along veins; moderately glossy. Venation pattern: Laciniate. Color: Developing leaves, upper surface: Close to 146A tinged with close to 152A; venation, close to 144A. Developing leaves, lower surface: Close to 177B. Fully expanded leaves, upper surface: Darker than between 139A and N189A; venation, close to 152A to 152B. Fully expanded leaves, lower surface: Close to 148B moderately to strongly tinged with close to 178A; venation, close to 152B. Petioles: Length: About 6.4 cm. Diameter: About 6 mm to 7 mm. Strength: Moderately strong, flexible. Texture and luster, upper and lower surfaces: Pubescent; moderately glossy. Color, upper surface: Close to 152B tinged with close to N170A; at the proximal base, close to 185A. Color, lower surface: Close to 152B tinged with close to 199A. Stipules: Quantity per leaf: Two. Length: About 1.6 cm. Width: About 1.7 cm. Shape: Broadly ovate. Apex: Bluntly acute. Base: Broadly cuneate. Margins: Entire, irregularly ciliate. Color, upper and lower surfaces: Close to 146C.

Flower description:

*Flowering habit*.—Rotate double sterile flowers arranged in axillary compound cymes; freely flowering habit with about nine flowers per cyme and about 180 flowers developing per plant during the flowering season; flowers face upright to outwardly.

*Fragrance*.—None detected.

*Natural flowering season*.—Long flowering period, plants flower freely and continuously from spring into the autumn in The Netherlands; during the winter in a greenhouse, plants begin flowering about 35 days after exposure to photoinductive treatments.

*Postproduction longevity*.—Individual flowers last about ten days on the plant; flowers not persistent; plants maintain good substance for about 20 to 30 days in an interior environment.

*Inflorescence height*.—About 15.9 cm.

*Inflorescence diameter*.—About 9 cm.

*Flower buds*.—Length: About 1.9 cm. Diameter, flattened: About 1.8 cm. Shape: Roughly circular; flattened. Texture and luster: Smooth, glabrous, slightly velvety; slightly glossy. Color: Close to between 145D and 150D; towards the margins and apex, close to 39B.

*Flowers*.—Diameter: About 4.1 cm. Depth: About 2.2 cm. Tepals: Quantity and arrangement: Four per flower arranged in two whorls. Length, lower tepals: About 3.1 cm. Width, lower tepals: About 3.7 cm. Length, upper tepals: About 2.4 cm. Width, upper tepals: About 2.8 cm. Shape: Roughly reniform. Apex: Rounded. Base: Reniform. Margin: Entire; slightly undulate. Texture and luster, upper surface: Smooth, glabrous, velvety; matte. Texture and luster, lower surface: Smooth, glabrous, velvety; matte to slightly glossy. Color, lower tepals: When opening, upper surface: Close to 38B; margins, close to 48A. When opening, lower surface: Close to 37A. Fully opened, upper surface: Close to 37B; margins, close to 48B; venation, close to between 50A and 53D;

color does not fade with development. Fully opened, lower surface: Close to 29C; center, close to 35B to 35C; venation, close to 151A to 151B; color does not fade with development. Color, upper tepals: When opening, upper surface: Close to between 37C and 38B; margins, close to 51B to 51C. When opening, lower surface: Close to 38D; towards the base, close to 145D; margins, close to between 47D and 51B. Fully opened, upper surface: Close to 38A; margins, close to 48B to 48C; venation, close to between 50A and 53C; color does not fade with development. Fully opened, lower surface: Close to 38C to 38D; margins, close to 48B to 48C; venation, close to 151A to 151B; color does not fade with development. Tepaloids: Quantity and arrangement: About 20 arranged in multiple whorls at the center of the flower. Length: About 1.4 cm to 1.8 mm. Width: About 9 mm to 18 mm. Shape: Obovate. Apex: Rounded to obtuse. Base: Cuneate. Margin: Entire; slightly undulate. Texture and luster, upper and lower surfaces: Smooth, glabrous, velvety; matte. Color: When opening, upper surface: Close to 150D; towards the margins and apex, close to 36C; margins, close to 51B. When opening, lower surface: Close to 150D; towards the margins and apex, close to 36B to 36C; margins, close to 51B. Fully opened, upper surface: Close to between 37B and 38B; margins, close to 51B; venation, similar to lamina colors; color does not change with development. Fully opened, lower surface: Close to between 36A and 38D; margins, close to 52C; venation, similar to lamina colors; color does not change with development.

*Peduncles*.—Length: About 7.6 cm. Diameter: About 5 mm to 7 mm. Angle: About 35° from lateral branch axis. Strength: Moderately strong; flexible. Texture and luster: Sparsely pubescent; moderately glossy. Color: Close to 146B to 146C.

*Pedicels*.—Length: About 3.1 cm. Diameter: About 3 mm. Angle: About 20° from the peduncle axis. Strength: Moderately strong; flexible. Texture and luster: Pubescent; glossy. Color: Close to 145A distally tinged with close to 153C.

*Flower bracts*.—Quantity and arrangement: Two per flower, opposite. Length: About 1.6 cm. Width: About 1.6 cm. Shape: Broadly ovate. Apex: Broadly acute. Base: Broadly cuneate. Margin: Entire, finely ciliate. Texture and luster, upper and lower surfaces: Smooth, glabrous; matte. Color, upper and lower surfaces: Close to 146C; towards the apex, tinged with close to 175A.

*Reproductive organs*.—None observed, all structures transformed into tepaloids.

*Seeds and fruits*.—Seed and fruit development have not been observed on plants of the new *Begonia* as flowers are sterile.

Pathogen & pest resistance: Resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'Bkpbeens' as illustrated and described.

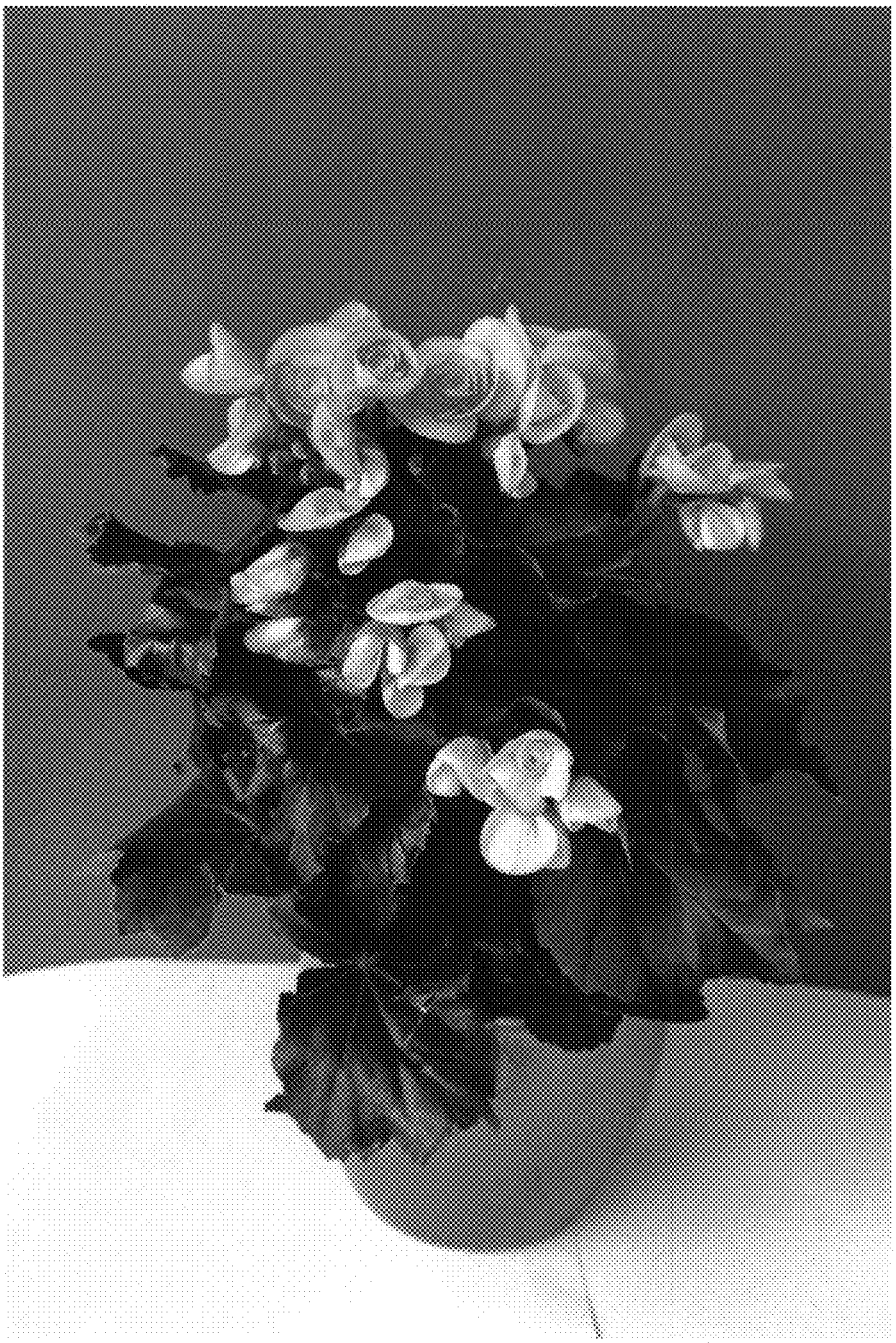

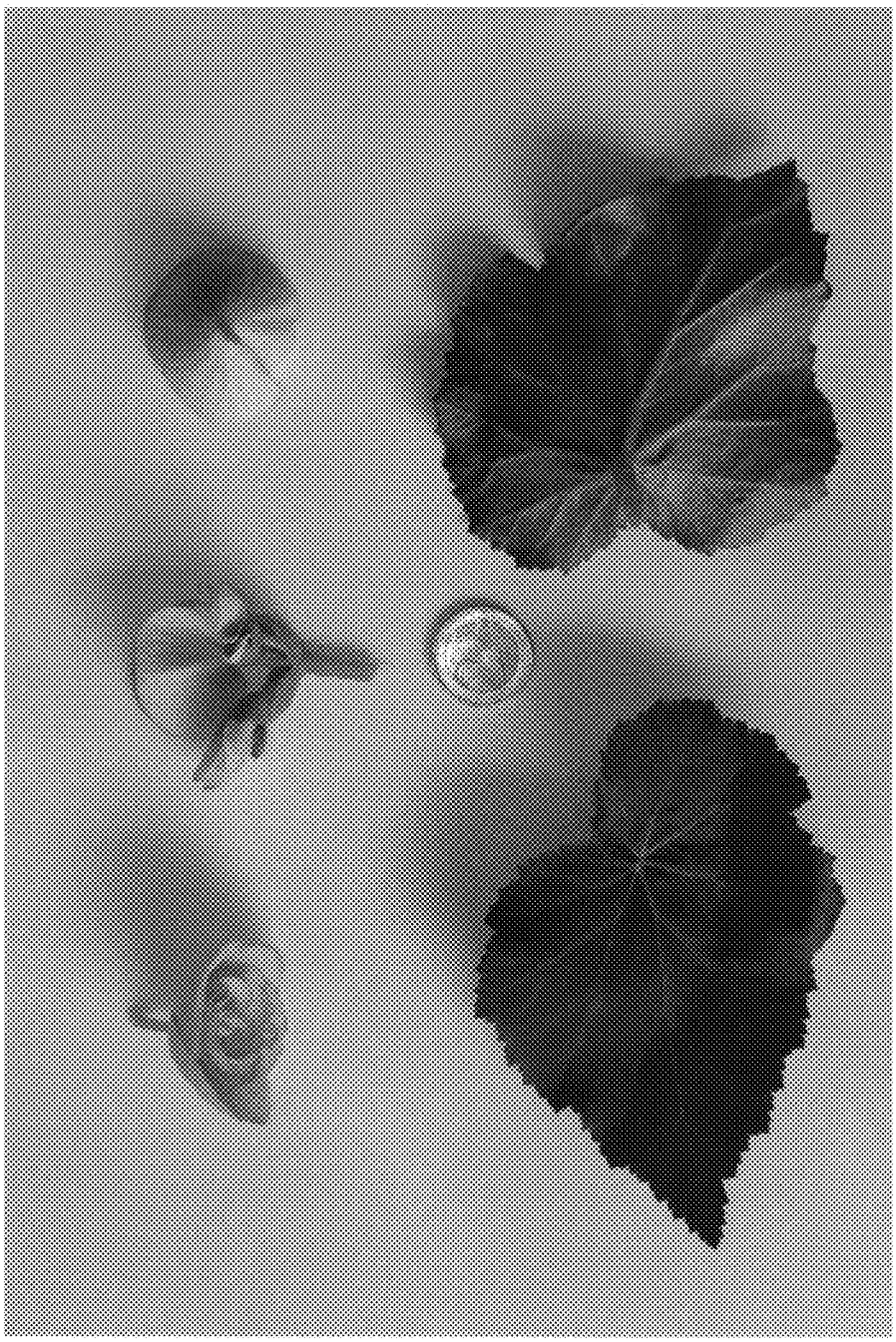

* * * * *